(12) United States Patent
Tsimerman

(10) Patent No.: US 11,972,861 B2
(45) Date of Patent: Apr. 30, 2024

(54) MACHINE LEARNING MODEL FOR ALLOCATION OF RESOURCES

(71) Applicant: Alexandr Tsimerman, RaAnana (IL)

(72) Inventor: Alexandr Tsimerman, RaAnana (IL)

( * ) Notice: Subject to any disclaimer, the term of this patent is extended or adjusted under 35 U.S.C. 154(b) by 829 days.

(21) Appl. No.: 17/100,988

(22) Filed: Nov. 23, 2020

(65) Prior Publication Data

US 2021/0398016 A1 Dec. 23, 2021

Related U.S. Application Data

(60) Provisional application No. 63/042,580, filed on Jun. 23, 2020.

(51) Int. Cl.
*G06N 20/00* (2019.01)
*G06F 18/214* (2023.01)
*G06F 18/25* (2023.01)
*G16H 40/20* (2018.01)

(52) U.S. Cl.
CPC ........... *G16H 40/20* (2018.01); *G06F 18/214* (2023.01); *G06F 18/254* (2023.01); *G06N 20/00* (2019.01)

(58) Field of Classification Search
CPC ...... G16H 40/20; G16H 50/80; G06F 18/214; G06F 18/254; G06N 20/00; G06N 3/044; G06N 3/08
See application file for complete search history.

(56) References Cited

U.S. PATENT DOCUMENTS

2019/0354850 A1* 11/2019 Watson .................. G06N 3/045
2021/0350271 A1* 11/2021 Ross ...................... G06N 20/00
2022/0083906 A1* 3/2022 Ong ....................... G06F 18/254

* cited by examiner

*Primary Examiner* — Hassan Mrabi

(57) ABSTRACT

There is provided a method for training a ML model ensemble, comprising: training a central ML model using training values of central location parameters of a central location, for sample resources: training a respective ML model using the remote location parameters for the respective sample resource, receiving a manual indication of allocation of the respective sample resource to the central location or the remote location, creating a main training dataset including the training values for the central locations, and the training values for the remote location parameters for each of the sample resources labelled with the manual indication, and training a main ML model using the training dataset for allocating a resource to central location(s) or to the respective remote location, wherein a subset of resources are allocated to respective remote locations and another subset of the resources are allocated to central location(s).

24 Claims, 7 Drawing Sheets

MACHINE LEARNING MODEL FOR ALLOCATION OF RESOURCES

RELATED APPLICATION

This application claims the benefit of priority under 35 USC § 119(e) of U.S. Provisional Patent Application No. 63/042,580 filed on 23 Jun. 2020, the contents of which are incorporated by reference as if fully set forth herein in their entirety.

FIELD AND BACKGROUND OF THE INVENTION

The present invention, in some embodiments thereof, relates to machine learning (ML) models and, more specifically, but not exclusively, to systems and methods for training and using a ML model for allocation of resources, for example, physical computational and/or network resources (e.g., processor(s), memory, data storage, network bandwidth), and/or virtual computational and/or virtual network resources (e.g., virtual memory, virtual processors, virtual data storage, and virtual network).

Examples of allocation of resources include, for example, determining an amount of network bandwidth to allocate to each one of multiple client terminals accessing a server, and the amount of network bandwidth to allocate to the server.

Technological tools, for example, neural networks, and statistical classifiers, are being developed for efficient allocation of resources. Such classifiers are trained on datasets of data labelled with a ground truth outcome, and are able to make predictions for a given set of input data, for efficiently allocating resources.

SUMMARY OF THE INVENTION

According to a first aspect, a computer implemented method of training a ML model ensemble for dynamic allocation of resources to a remote location or to a central location, comprises: receiving a plurality of training values for a plurality of central location parameters of the central location, training a central ML model using the training values for the plurality of central location parameters, for each of a plurality of sample resources: receiving training values for a plurality of remote location parameters, training a respective ML model using the plurality of remote location parameters for the respective sample resource, receiving a manual indication of allocation of the respective sample resource to the central location or the remote location, creating a main training dataset including the plurality of training values for the plurality of central locations, and the training values for the plurality of remote location parameters for each of the plurality of sample resources labelled with the manual indication, and training a main ML model using the training dataset for allocating a resource to at least one central location or to the respective remote location, wherein a subset of a plurality of resources are allocated to respective remote locations and another subset of the plurality of resources are allocated to at least one central location.

According to a second aspect, a computer implemented method of dynamic allocation of a plurality of resources to a plurality of remote location or at least one central location using an ensemble of machine learning (ML) models, comprises: receiving, as an outcome of a central ML model, a prediction of a plurality of central location parameters of the at least one central location, wherein the central ML model is trained on a central training dataset of historic dynamically adjusted central location parameters, iterating for each respective resource of the plurality of resources: receiving, as an outcome of a respective remote ML model of a plurality of remote ML models, a prediction of a plurality of remote location parameters of a certain remote location, wherein each respective remote ML model corresponds to a respective resource and to one certain remote location, wherein the respective remote ML model is trained on a respective remote training dataset of historic remote location parameters, inputting the plurality of central location parameters of the at least one central location and the plurality of remote location parameters of the certain remote location of the respective resource into a main ML model, and obtaining, as an outcome of the main ML model, an allocation of the respective resource to the remote location or to the at least one central location for at least one future time interval, wherein a subset of a plurality of resources are allocated to respective remote locations and another subset of the plurality of resources are allocated to at least one central location, wherein the main ML model is trained on a main training dataset including: training values for the plurality of central location parameters of the central location, and for each of a plurality of sample resources, training values for the plurality of remote location parameters, and corresponding labels of allocation to the remote location or to the central location for each of at least one historical time intervals.

According to a third aspect, a system for dynamic allocation of a plurality of resources to a plurality of remote location or at least one central location using an ensemble of machine learning (ML) models, comprises: at least one hardware processor executing a code for: receiving, as an outcome of a central ML model, a prediction of a plurality of central location parameters of the at least one central location, wherein the central ML model is trained on a central training dataset of historic dynamically adjusted central location parameters, iterating for each respective resource of the plurality of resources: receiving, as an outcome of a respective remote ML model of a plurality of remote ML models, a prediction of a plurality of remote location parameters of a certain remote location, wherein each respective remote ML model corresponds to a respective resource and to one certain remote location, wherein the respective remote ML model is trained on a respective remote training dataset of historic remote location parameters, inputting the plurality of central location parameters of the at least one central location and the plurality of remote location parameters of the certain remote location of the respective resource into a main ML model, and obtaining, as an outcome of the main ML model, an allocation of the respective resource to the remote location or to the at least one central location for at least one future time interval, wherein a subset of a plurality of resources are allocated to respective remote locations and another subset of the plurality of resources are allocated to at least one central location, wherein the main ML model is trained on a main training dataset including: training values for the plurality of central location parameters of the central location, and for each of a plurality of sample resources, training values for the plurality of remote location parameters, and corresponding labels of allocation to the remote location or to the central location for each of at least one historical time intervals.

In a further implementation of the first, second, and third aspects, further comprising updating the training datasets using at least one member of a group comprising of: (i)

inserting a previous outcome of the central ML model as input into at least one of the plurality of remote training datasets for updating training of the respective remote ML model, (ii) inserting a previous outcome of the main ML model as input into at least one of the plurality of remote training datasets for updating training of the respective remote ML model, (iii) inserting one or more previous outcomes of one or more remote ML models as input into at least one other remote training datasets for updating training of the respective remote ML model, (iv) inserting a previous outcome of one or more remote ML models as input into the central training datasets for updating training of the central ML model, (v) inserting a previous outcome of the main ML model as input into the central training datasets for updating training of the central ML model, (vi) inserting a previous outcome of the main ML model as current input into the main training datasets for updating training of the main ML model, (vii) inserting a previous outcome of the respective remote ML model as current input into the respective remote training datasets for updating training of the remote ML model, and (viii) inserting a previous outcome of the central ML model as current input into the central training datasets for updating training of the central ML model.

In a further implementation of the first, second, and third aspects, each remote location is allocated no more than a single sample resource, and the central location is allocated a plurality of sample resources.

In a further implementation of the first, second, and third aspects, further comprising at least one member of a group comprising of: (i) feeding a previous outcome of the central ML model as input into at least one of the plurality of remote ML models for generating the respective outcome of the respective remote ML model, (ii) feeding a previous of the main ML model as input into at least one of the plurality of remote ML models for generating the respective outcome of the respective remote ML model, (iii) feeding one or more previous outcomes of one or more remote ML models as input into at least one other remote ML models for generating the respective outcome of the respective remote ML model, (iv) feeding a previous outcome of one or more remote ML models as input into the central ML model for generating the outcome of the central ML model, (v) feeding a previous outcome of the main ML model as input into the central ML model for generating the outcome of the central ML model, (vi) feeding a previous outcome of the main ML model as current input into the main ML model for generating the outcome of the main ML model, (vii) feeding a previous outcome of the respective remote ML model as current input into the respective remote ML model for generating the outcome of the remote ML model, and (viii) feeding a previous outcome of the central ML model as current input into the central ML model for generating the outcome of the central ML model.

In a further implementation of the first, second, and third aspects, each remote location is allocated no more than a single resource of the plurality of resources, and the central location is allocated a plurality of sample resources.

In a further implementation of the first, second, and third aspects, further comprising, allocating the respective resource to the remote location or to the at least one central location according to the outcome of the main ML model.

In a further implementation of the first, second, and third aspects, the features of the method are dynamically iterated using updated plurality of central location parameters and/or plurality of remote location parameters, for additional future time intervals.

In a further implementation of the first, second, and third aspects, at least one of the plurality of central location parameters and the plurality of remote location parameters comprises a time sequence of values for each of a plurality of historical time intervals.

In a further implementation of the first, second, and third aspects, the main ML model comprises a plurality of sub-ML models, each trained on a respective training dataset of a respective central location and corresponding plurality of remote locations, wherein the inputting is into the respective sub-ML models and the outcome is of the respective sub-ML models.

In a further implementation of the first, second, and third aspects, further comprising: receiving an indication of a manual adjustment to the allocation for the respective resource by the outcome of the ML model, creating a training record, using the respective plurality of central location parameters of the central location, the plurality of remote location parameters of the certain remote location of the respective resource, and a label comprising the manual adjustment, and updating the ML model using the training record.

In a further implementation of the first, second, and third aspects, the allocation of the respective resource is for each of a plurality of time intervals In a further implementation of the first, second, and third aspects, further comprising: receiving, as an outcome of the central ML model, at least one global constraint as a certain central location parameter, the at least one global constraint denoting a constraint on the plurality of resources allocated to the central location for the at least one future time interval, inputting the at least one global constraint into the main ML model, wherein the allocation of the subset of the plurality of resources satisfies the constraint.

In a further implementation of the first, second, and third aspects, the plurality of remote location parameters for the central location of each of the plurality of resources are inputted as a combination, with the at least one global constraint and with the plurality of central location parameters, into the main ML model.

In a further implementation of the first, second, and third aspects, the at least one global constraint comprises a physical distancing requirement during a viral disease outbreak defining at least one of: a maximal density of resources at the central remote location, minimal distance between resources at the central remote location, maximal total number of resources at the central remote location, and maximal number of resources per room at the central remote location.

In a further implementation of the first, second, and third aspects, the at least one global constraint comprises at least one member selected from the group consisting of: maximal number of resources at the central location, and compatibility between resources.

In a further implementation of the first, second, and third aspects, further comprising: receiving, for the respective resource as an outcome of the respective remote ML model, at least one constraint on the respective resource allocated to the central location or to the remote location for the at least one future time interval, inputting the at least one constraint into the main ML model, wherein the allocation of the respective resource satisfies the constraint.

In a further implementation of the first, second, and third aspects, the at least one constraint is selected from the group consisting of: number of remaining compulsory remote location time intervals.

In a further implementation of the first, second, and third aspects, the allocation of the respective resource comprises a numerical score indicative of a ranking likelihood of being allocated to the remote location or to the central location, wherein resources not allocated to the remote location or to the central location are placed on a waiting list according to the numerical score.

In a further implementation of the first, second, and third aspects, further comprising: receiving, for the respective resource as an outcome of the respective remote ML model, request for allocation to the remote location or the central location for the at least one future time interval, wherein inputting further comprises inputting the request for allocation into the main ML model, wherein the main ML model computes the allocation for meeting the request.

In a further implementation of the first, second, and third aspects, further comprising receiving at least one additional data parameters for the respective resource, wherein the additional data is inputted into the main ML model, the at least one additional data parameters selected from the group consisting of: number of accepted and/or declined allocations to a request, number of accepted and/or declined allocated to the request from a waiting list, number and/or time intervals of historical requests, pendency between the request and being granted the request, number of historical requests that were met, number of lack of meeting the request due to external factors.

In a further implementation of the first, second, and third aspects, further comprising: receiving, at least one scheduled event planned for a certain future time interval independent of the central location, the at least one schedule event impacting a plurality of resources, wherein inputting further comprises inputting the at least one scheduled event into the main ML model, wherein the ML model computes the allocation for meeting the at least one scheduled event.

In a further implementation of the first, second, and third aspects, further comprising: extracting a plurality of extracted features from at least one of the plurality of central location parameters, and the plurality of remote location parameters, wherein inputting comprises inputting at least the plurality of extracted features into the ML model.

In a further implementation of the first, second, and third aspects, the at least one global constraint comprises planned future meetings scheduled to occur in the central location.

In a further implementation of the first, second, and third aspects, a subset of central location parameters of the central location are selected from the group consisting of: costs associated with the central location, costs associated with each resource at the central location, and wherein the ML model computes the allocation for reducing the subset of central location parameters, and further comprising: generating a recommendation for obtaining the reduction of the subset of central location parameters by the computed allocation.

In a further implementation of the first, second, and third aspects, a subset of plurality of remote location parameters include a resource profile including at least one resource specific parameter of the resource associated with the respective remote location, selected from the group consisting of: seniority, tenure, salary, insurance data, commute cost data, gender, age, marital status, number of children, ages of children, demographic information, salary, and the like.

In a further implementation of the first, second, and third aspects, further comprising receiving, for the respective resource, an indication of productivity at the remote location and/or at the central location, wherein inputting further comprises inputting the indication of productivity at the central location and/or the remote location into the main ML model, wherein the ML model computes the allocation for maximizing productivity at the remote location and/or central location.

In a further implementation of the first, second, and third aspects, at least one of the central location parameters of the central location includes an indication of team groups of subsets of the resources, birthday or special event of one of the subset of resources of a certain team group, and wherein the ML model computes the allocation for allocation at many of the subset of resources of each team group to the central location during a same time interval.

In a further implementation of the first, second, and third aspects, at least one of the plurality of remote location parameters of the respective remote location is selected from the group consisting of: distance from the respective remote location to the central location, historical estimated commute time from the remote location to the central location, predicted future commute time from the respective remote location to the central location, and preferred mode of transport.

In a further implementation of the first, second, and third aspects, at least one of the plurality of central location parameters of the central location is selected from the group consisting of: canteen menu, special event time intervals.

In a further implementation of the first, second, and third aspects, the resources are, for example, contractors, sub-contractors, part time employees, and/or full time employees of a company, wherein the central location comprises an office of the company, and wherein the remote location comprises a home of the respective resource, wherein the allocation is for working at the office or at home.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
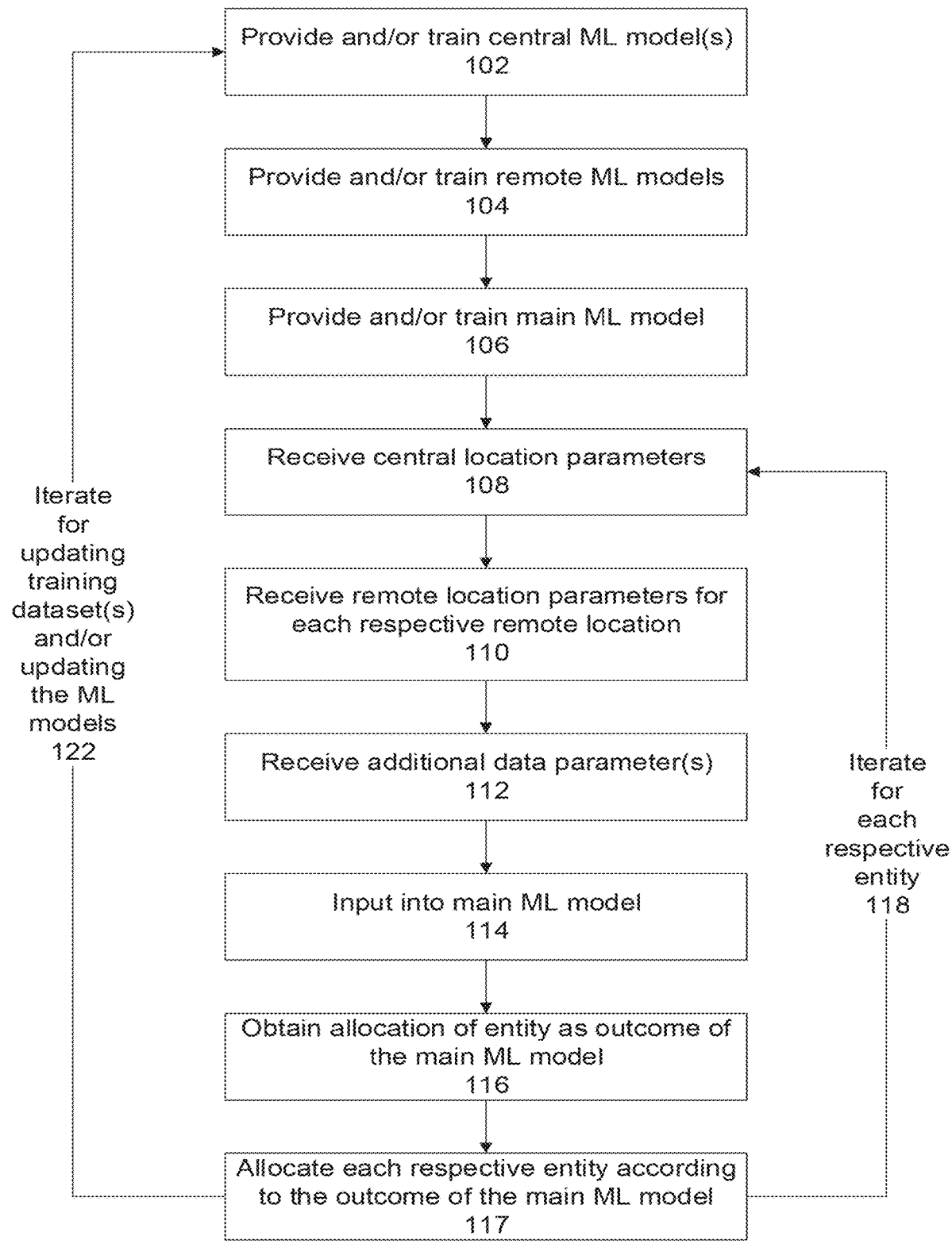
FIG. 1 is a flowchart of a method for using an ensemble of ML models for allocation of resources to a remote location or a central location, in accordance with some embodiments of the present invention.

The present invention, in some embodiments thereof, relates to machine learning (ML) models and, more specifically, but not exclusively, to systems and methods for training and using a ML model for allocation of resources.

An aspect of some embodiments of the present invention relates to systems, methods, an apparatus, and/or code instructions (i.e., stored on a memory and executable by one or more hardware processors) for dynamic allocation of resources to multiple remote locations and/or to one or more central locations, using an ensemble of ML models. For example, allocation of networking resources (e.g., bandwidth, routers) between a server and clients, allocation of virtual resources between a virtual server (e.g., virtual machine manager, hypervisor) and virtual clients (e.g., virtual machines), sub-processors and a main processor (which may be physical and/or virtual), between Internet of Things (IoT) devices and a server communicating with the IoT devices, and allocation of memory between a main process executing on a processor and client processes executing on the processor and/or other processors. In another example, dynamic allocation of people, such as employees, to working from home (i.e., remote location), or in one or more offices (i.e., central locations).

Optionally, a single resource is located at each respective remote location, for example, a single client terminal, a single IoT device, a single virtual client terminal, a single virtual processor, and a single employee. Each respective remote location may be allocated a single resource, i.e., a maximum of one resource may be allocated for each respective remote location. Each single resource may be assigned other resources for use only by the single resource, for example, bandwidth, memory, and processor utilization (e.g., physical and/or virtual). Each respective remote location may be physically and/or virtually separated from other remote locations and/or from the central location(s). For example, each single client terminal is located at a remote geographic location, communicating with a central server over a network connection. In another example, each single virtual client terminal is logically separated from other virtual client terminals and from the hypervisor. In yet another example, each employee is located in their own home. The single entities at the respective remote locations may communicate with the central location(s).

Optionally, multiple resources may be located at the central location (e.g., at each respective central location), for example, multiple client terminals (e.g., physical and/or virtual), multiple processors (e.g., physical and/or virtual), and/or a server serving multiple client terminals (e.g., physical and/or virtual), and multiple employees. Each central location may be allocated multiple resources, i.e., two or greater. It is noted that no resources may be necessarily allocated to the central resources (e.g., on a certain day), and/or a single resource may be allocated to the central resource, in which case the central resource has the potential to be allocated additional resources. The maximal number of resources allocated to the central location may be, for example, unlimited (e.g., undefined) and/or defined (e.g., as a constraint). The multiple resources may interact with one another at the central location, for example, sharing of a common pool of resources allocated to the central location. In another example, employees at the central location may work as a team. For example, processors used by a central server at the central location share a pool of memory and/or bandwidth allocated to the central server. In another example, employees at the central location may attend a common meeting.

A central ML model generates an outcome of multiple central location parameters of the at least one central location. The central ML model is trained on a central training dataset of historic dynamic adjusted location parameters. The central ML model may be dynamically updated with manual corrections to the generated outcomes, for example, indicating when the outcome of the central ML model is incorrect. The central ML model may sometimes be referred to herein as a virtual administrator (and/or virtual employer) that makes decisions regarding the central location (e.g., office). The central training dataset may be generated, for example, based on actual historical decisions made by a human administrator (e.g., network manager, office manager). The central ML model predicts, for example, future decisions and/or preferences that would otherwise be made by the human administrator, for example, allocation of networking and/or virtual resources between a central location (physical and/or virtual) and remote locations (physical and/or virtual), and in another example, maximum number of people allowed to work in the office on a given day, and type of food served that day.

A respective remote ML model is generated for each remote location and/or corresponding to each resource. The respective remote ML model may sometimes be referred to herein as a virtual resource (and/or virtual employee), predicting for example, preferences and/or selections that would otherwise be made by the corresponding resource (e.g., person, employee). Each respective remote ML model generates an outcome of multiple remote location parameters for its respective corresponding remote location and/or resource corresponding to the remote location. Each respective remote ML model is trained on a respective remote training dataset of historic remote location parameters, which may include a profile of the resource, for example, constraints, and/or preferences of the resource. Each respective remote ML model may be dynamically updated with manual corrections to the generated outcomes, for example, indicating when the outcome of the respective remote ML model is incorrect. Each respective remote training dataset may be generated, for example, based on actual historical decisions made by a respective human resource (e.g., employer). Each respective remote ML model predicts, for example, future decisions and/or preferences that would otherwise be made by the human employee, for example, preference for when to work from home and when to work from the office, commute time to work from the office, and request to work with other team members from the office on the same day.

For each respective resource, the central location parameters of the at least one central location obtained from the central ML model and the plurality of remote location parameters of the respective remote location corresponding to the respective resource obtained from the respective remote ML model, are inputted into a main ML model. The inputting may be done per resource, and/or as a feature vector created for multiple (e.g., all or subset of) resources.

The main ML model provides an outcome of an allocation of the respective resource to the remote location or to the at least one central location for at least one future time interval, for example, per day for the upcoming week. Each of multiple resources is allocated either to a respective remote location, or to the at least one central location. For example, for the employees of a company, each employee is allocated either to work from home or to work from the office, for example, for each day of the upcoming week, for vacation days, statutory holidays, sick leave, and/or maternity/paternity leave. The main ML model is trained on a main training dataset including training values for the central location parameters of the central location which may be obtained as an outcome of the central ML model (and optionally manually corrected as described herein), and for each of multiple sample resources, training values for the remote location parameters which may be obtained as an outcome of the respective remote ML model (and optionally manually corrected as described herein), and corresponding labels of allocation to the remote location or to the central location for each historical time interval.

Optionally, previous outcomes of one or more ML models of the ensemble are fed as input into other ML models and/or into the same ML model for generating the current outcomes. One or more combinations may be implemented, for example:

Feeding a previous outcome of the central ML model as input into at least one of the remote ML models for generating the respective outcome of the respective remote ML model.

Feeding a previous of the main ML model as input into at least one of the remote ML models for generating the respective outcome of the respective remote ML model.

Feeding one or more previous outcomes of one or more remote ML models as input into at least one other remote ML models for generating the respective outcome of the respective remote ML model.

Feeding a previous outcome of one or more remote ML models as input into the central ML model for generating the outcome of the central ML model.

Feeding a previous outcome of the main ML model as input into the central ML model for generating the outcome of the central ML model.

Feeding a previous outcome of the main ML model as current input into the main ML model for generating the outcome of the main ML model.

Feeding a previous outcome of the respective remote ML model as current input into the respective remote ML model for generating the outcome of the remote ML model.

Feeding a previous outcome of the central ML model as current input into the central ML model for generating the outcome of the central ML model.

Optionally, previous outcomes of one or more ML models of the ensemble are inputted into training datasets used to train other ML models and/or into the training dataset of the same ML model for updating the respective training datasets for updating training and/or retraining of the respective ML model using the updated training dataset.

The resources may for example, computer related and/or network related resources, which may be physical (e.g., hardware) and/or virtual resources (e.g., virtual memory, virtual storage, virtual processors, virtual functions, virtual memory), for example, laptop computers, projectors, network bandwidth, servers, specialized processing hardware, memory, storage, standard processor(s), computing devices, and the like, which are optimally allocated to either one or more central locations and/or to respective remote locations.

In one example, the resources data, such as files and/or executable code, that are to be stored. The remote locations are remote storage facilities (e.g., of individual) users, for example, client terminals, mobile devices, and the like. The central locations are cloud storage facilities. The allocation by the main ML model is whether to store each respective data (e.g., file) in the remote storage facility or the cloud storage. The remote and/or central location parameters may be, for example, a prediction of: storage space occupied by the file and/or code, rate of access to the file and/or code, type of file and/or code (e.g., streaming, download, establish continuous data transfer session), processor utilization to handle the file and/or code, memory utilization to handle the file and/or code, loading time for a device to receive the file and/or code being accessed, and bandwidth requirements to transfer the file and/or code to an external entity accessing the file and/or code. The remote and/or central location parameters may be generated as outcomes by respective remote and/or central ML models based on inputs, which may be currently available and/or historical, for example, available processor resources, available memory, available bandwidth, history of storage of files and/or code, history of access to stored files and/or code, and the like. Examples of constraints for the allocation include: user selected preferences to store the file locally or in the cloud storage.

In another example, the resources may be people that are allocated to work at home or to work from a central office location, for example, during viral infection outbreaks such as COVID-19 where social distancing and/or other gathering rules are applied to reduce and/or prevent spread of the viral infection.

In at least some embodiments, the ensemble of the ML models, including the central ML model, the multiple remote ML models, and the main ML model, provide a machine learning architecture that provides an optimal allocation of resources to the remote and/or central location, which may be dynamically updated as conditions at the remote and/or central location change. The dynamic generation of outcomes of teach ML model, and interaction between ML models using the outcomes of the ML models, provides the optimal allocation of resources. Optionally, the interactions that arise by feeding previous outcome(s) of one ML model of the ensemble (e.g., a remote ML model, the central ML model, and/or the main ML model) as input into one or more other ML models and/or into the same ML model, generates a synergistic environment where each ML model learns over time from itself and/or other ML models, thereby responding to dynamic changes in the remote and/or central location(s). For example, in comparison to using a single ML model that receives input and generates the allocation outcome, using the central ML model and the multiple remote ML models enables optimal allocation in a complex environment with a very large number of parameters and a very large number of possible allocations that may be made, which may dynamically change over time, for example, based on each remote ML model generating its own predictions, and the central ML model generating predictions, which are then used by the main ML model to perform the allocations.

At least some implementations of the systems, methods, apparatus, and/or code instructions described herein relate to the technical problem of dynamic allocating of resources to a remote location or to a central location in a dynamic environment where parameters change over time, for example, allocation of physical computational resources (e.g., hardware acceleration cards, special processors, data storage devices), virtual computer resources (e.g., virtual memory, virtual storage, virtual functions, virtual processor(s), virtual network) between remote clients and central server(s). The amount of resources used at the central and/or remote parameter(s) may change over time, for example, changes in required processor utilization and/or amount of memory, changes in hardware type (e.g., upgrades), changes in implemented protocols, changes in supported features (e.g., by virtual drivers), and/or changes in network performance (e.g., delay, error rate, bandwidth). What is optimal during one time interval may not necessarily be optimal during another time interval due to the dynamic changes. In another example, allocation of employees of a company to work from home or to work from an office of the company.

At least some implementations of the systems, methods, apparatus, and/or code instructions descried herein relate to the technical problem of improving the optimal allocation of resources, for example, to provide a higher overall performance of the allocated resources (i.e., aggregated performance of the individual resources), to provide a higher performance of each allocated resources, and/or to perform the allocation of resources for meeting many as possible (or all) constraints such as requests to allocation of the resource to the central and/or remote locations. Optimization problems are complex, due to the large number of inputs and large number of possible combinations, which yield different results. Finding the optimal solution, for example, by brute force methods that evaluation each possible combination, may be impossible to perform in a reasonable amount of time using a reasonable amount of available computational resources.

At least some implementations of the systems, methods, apparatus, and/or code instructions described herein improve the technology of ML architectures for allocation of resources, by computing the central ML model, and the remote ML models, which are customized for the central and remote locations by training on training datasets created for each respective central and/or remote location. The central ML models and the remote ML models, which are each created for a different respective location using data associated with that respective location, improve the allocation ability of the main ML model, to provide the higher performance of the allocated resources, higher overall performance, and/or meeting as many constraints as possible. The allocation is performed to obtain a better optimization of allocation relative to other approaches, in a reasonable amount of time and/or with reasonable computational resources.

At least some implementations of the systems, methods, apparatus, and/or code instructions described herein improve over standard approaches, for example, manual approaches, and/or automated approaches that use sets of rules and/or machine learning architectures, for example, that use a single model (e.g., single neural network). Manual approaches and/or sets of rules and/or single models usually do not result in the most optimal solution, in particular when constraints are imposed, since it is impossible for such approaches to evaluate the large number of potential combinations of different available input parameters. Such decisions are usually made simply, resulting in a non-optimal result.

In at least some implementations, the ensemble of the ML models, including the central ML model, the multiple remote ML models, and the main ML model, provide a machine learning architecture that provides an optimal allocation of resources to the remote and/or central location. The dynamic generation of outcomes of teach ML model, and interaction between ML models using the outcomes of the ML models, provides the optimal allocation of resources. For example, in comparison to using a single ML model that receives input and generates the allocation outcome, using the central ML model and the multiple remote ML models enables optimal allocation in a complex environment with a very large number of parameters and a very large number of possible allocations that may be made, for example, based on each remote ML model generating its own predictions, and the central ML model generating predictions, which are then used by the main ML model to perform the allocations.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the terms resources and entities may sometimes be interchanged.

ML models described herein may be implemented, for example, as recurrent neural networks (RNN) which may be designed to encode time sequence data into a state, deep neural networks, other neural network architectures (e.g., fully connected, encoder-decoder, recursive neural network, uni- and bi-directional long-short term memory networks, gated recurrent unit network, convolutional), and/or other architectures such as support vector machines (SVM), logistic regression, linear classifier, time series classifier (e.g., ARIMA, SARIMA, SARIMAX, and exponential smoothing), k-nearest neighbor, decision trees, gradient boosting, random forest, and combinations of the aforementioned. When using a neural network, a constraint (as used herein) and/or conflict (e.g., two resource allocations where only once can be made) may be implemented, for example, by a significantly larger penalty relative to other non-constraint penalties. It is noted that disobedience of a preference (e.g., as used herein) is also a penalty, but significantly smaller in comparison to the disobedience of a constraint and/or conflict. The neural network may be unable to satisfy all constraints and/or requests and/or avoid all conflicts, in which case the outcome is provided by easing the penalty of a certain constraint in order to obtain an outcome solution.

Figure 2:
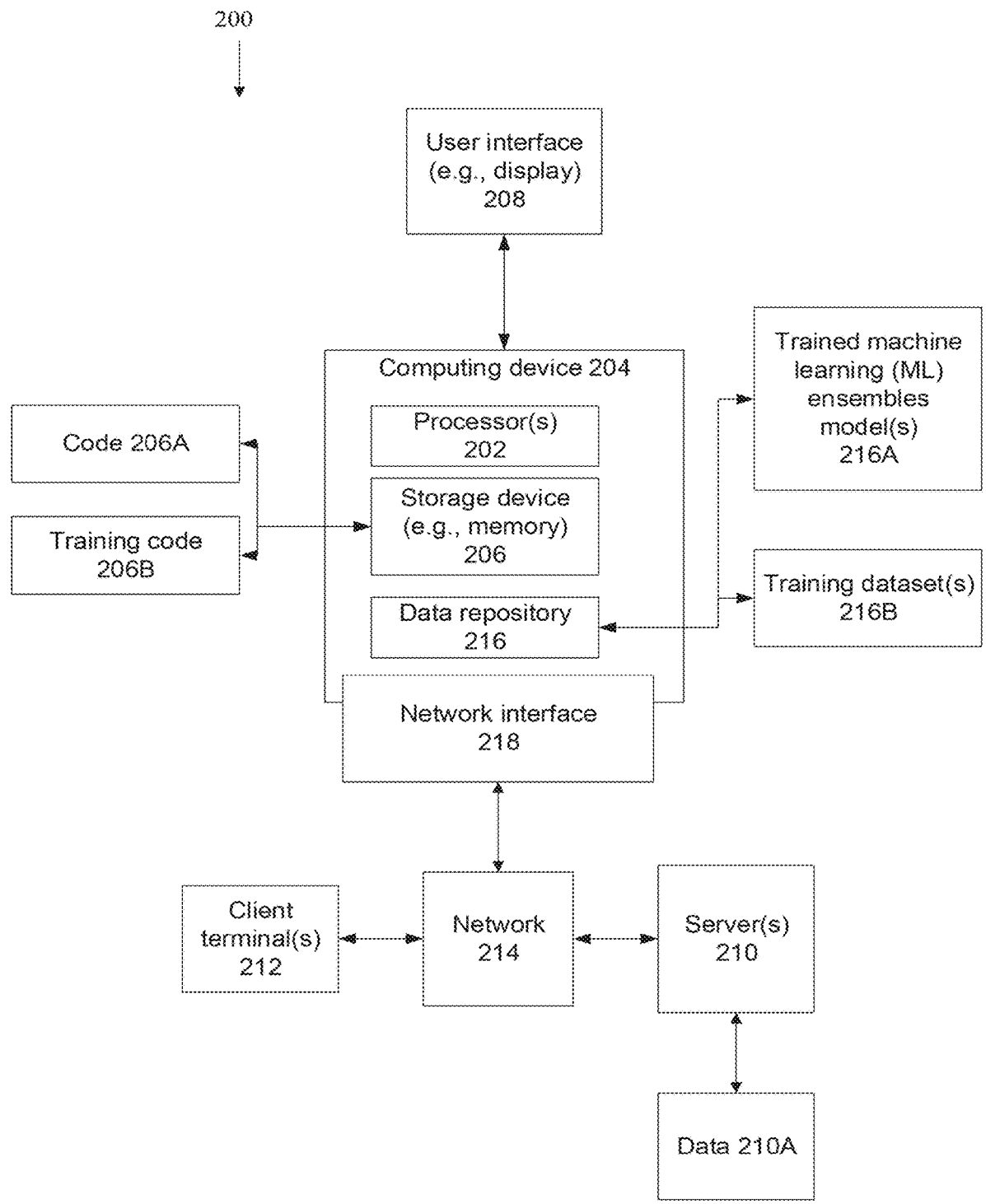
FIG. 2 is a block diagram of a system for training the ML model ensemble and/or using the ML model ensemble for allocation of resources to a remote location or a central location, in accordance with some embodiments of the present invention.
Figure 3:
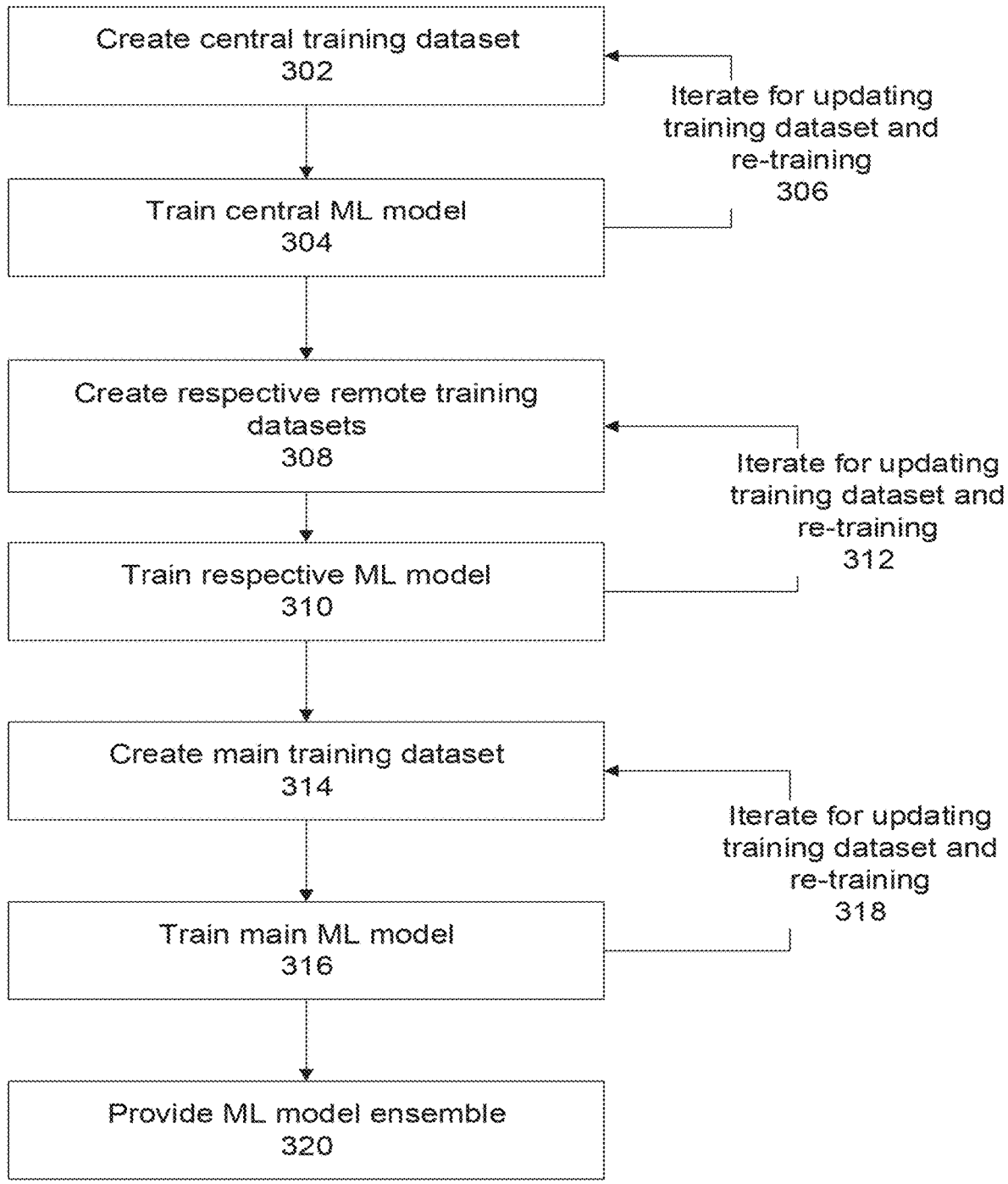
FIG. 3 is a flowchart of a method for training the ML model ensemble for allocation of resources to a remote location or a central location, in accordance with some embodiments of the present invention.

Reference is now made to FIG. 1, which is a flowchart of a method for using an ensemble of ML models for allocation of resources to a remote location or a central location, in accordance with some embodiments of the present invention. Reference is also made to FIG. 2, which is a block diagram of a system 200 for training the ML model ensemble and/or using the ML model ensemble for allocation of resources to a remote location or a central location, in accordance with some embodiments of the present invention. Reference is now made to FIG. 3, which is a flowchart of a method for training the ML model ensemble for allocation of resources to a remote location or a central location, in accordance with some embodiments of the present invention. Reference is also made to FIGS. 4A-4D, which are flowcharts of an exemplary process for allocation of resources to a remote location or to a central location, in accordance with some embodiments of the present invention. System 200 may implement the acts of the method described with reference to FIGS. 1, FIG. 3 and/or FIGS. 4A-D, by processor(s) 202 of a computing device 204 executing code instructions 206A stored in a storage device 206 (also referred to as a memory and/or program store).

Examples of inputs and/or outputs are described with reference to Examples 1 and 2 below.

Multiple architectures of system 200 based on computing device 204 may be implemented. In an exemplary implementation, computing device 204 storing code 206A may be implemented as one or more servers (e.g., network server, web server, a computing cloud, a virtual server) that provides services (e.g., one or more of the acts described with reference to FIG. 1 and/or 3) to one or more client terminals 212 over a network 214, for example, providing software as a service (SaaS) to the client terminal(s) 212, providing software services accessible using a software interface (e.g., application programming interface (API), software development kit (SDK)), providing an application for local download to the client terminal(s) 212, and/or providing functions using a remote access session to the client terminals 212, such as through a web browser. For example, multiple users use their respective client terminals 212 to subscribe to services that are centrally provided by computing device 204. Each user may represent, for example, a manager of a group of people, where the manager is in charge of allocating the people (e.g., employees) to respective remote locations (e.g., to work in their homes) or to the central location (e.g., to work in the office). The computed allocations of people to the central and remote locations is provided to the respective client terminals 212 by computing device 204. ML model 216A of computing device 204 may include a master ML model and/or ensemble of sub-ML models, each trained using training datasets of different groups of people with optionally different locations, for example, different departments of the same company and/or different companies. The master ML model and/or ML model ensemble may provide centralized services to different users, for example, managers of different departments and/or different companies. In another example, computing device 204 may include locally stored software (e.g., code 206A) that performs one or more of the acts described with reference to FIG. 1 and/or 3, for example, as a self-contained client terminal that is designed to be used by users of the client terminal.

In another example, each client terminals 212 may obtain their respective ML model ensemble 216A, which may be customized, from computing device 204 (which may compute and/or update ML model ensemble 216A as described herein) for local installation and use. Alternatively, ML model ensemble 216A may be locally trained by each client terminal 212. Each client terminal 212 may store its own custom computed trained ML model ensemble 216A for local use. For example, code 206A is loaded on a computer used by the manager. The ML model may be trained using a training dataset of data of people managed by the manager. In such implementation, each client terminal of each manager may execute its own code 206A using its own customized ML model ensemble 216A.

Each ML model ensemble 216A includes the central ML model(s), the multiple remote ML model(s), and the main ML model, as described herein.

Processor(s) 202 of computing device 204 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include a single processor, or multiple processors (homogenous or heterogeneous) arranged for parallel processing, as clusters and/or as one or more multi core processing devices.

Data storage device 206 stores code instructions executable by processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Storage device 206 stores code 206A that implements one or more features and/or acts of the method described with reference to FIG. 1 and/or training code 206B that implements one or more features and/or acts of the method described with reference to FIG. 3 when executed by processor(s) 202.

Computing device 204 may include a data repository 216 for storing data, for example one or more of: ML model(s) 216A, which is computed and/or updated as described herein, and/or training datasets 216B that store data for training and/or updating ML model 216A. Data repository 216 may be implemented as, for example, a memory, a local hard-drive, virtual storage, a removable storage unit, an optical disk, a storage device, and/or as a remote server and/or computing cloud (e.g., accessed using a network connection).

Network 214 may be implemented as, for example, the internet, a local area network, a virtual private network, a wireless network, a cellular network, a local bus, a point to point link (e.g., wired), and/or combinations of the aforementioned.

Computing device 204 may include a network interface 218 for connecting to network 214, for example, one or more of, a network interface card, a wireless interface to connect to a wireless network, a physical interface for connecting to a cable for network connectivity, a virtual interface implemented in software, network communication software providing higher layers of network connectivity, and/or other implementations.

Computing device 204 may connect using network 214 (or another communication channel, such as through a direct link (e.g., cable, wireless) and/or indirect link (e.g., via an intermediary computing unit such as a server, and/or via a storage device) with server(s) 210, from which at least some of the data 210A that is fed into ML model 216A and/or included in training dataset(s) 216B for training ML model 216A may be obtained. Client terminal(s) 212, which may be used by users remotely accessing computing device 204, as described herein.

Data 210A may be the remote location parameters and/or central location parameters and/or additional data parameters described herein. Data 210A may be collected, for example, via an API, via sensors, via code sensors, extracted from other data (e.g., using natural language processing methods, data from a database), and/or manually provided by a user.

Computing device 204 and/or client terminal(s) 212 include and/or are in communication with one or more physical user interfaces 208 that include a mechanism for a user to enter data and/or view data (e.g., enter at least some data that is fed into the ML model, and/or view the computed allocations), optionally within a GUI. Exemplary user interfaces 208 include, for example, one or more of, a touchscreen, a display, a keyboard, a mouse, and voice activated software using speakers and microphone.

Referring now back to FIG. 1, in one example, the resources are employees of a company, the central location(s) include an office(s) of the company, and the remote location(s) are respective homes of the resources. The allocation is for each employee, to be working at the office or at home. In another example, the resources are computer and/or network resources, for example, laptop computers, projectors, servers, and network bandwidth. The allocation is for each resource, to be assigned to a remote location (e.g., where a single user is using that resource) and/or to a central location (e.g., where multiple users are using that resource).

At 102, the central ML model is provided and/or trained on a central training dataset of historic dynamically adjusted central location parameters. The historic dynamically adjusted central location parameters may be represented, for example, a time sequence of values of the respective location parameter, which varies over time. In another example, the historic dynamically adjusted central location parameter may be represented, for example, as a value of the respective central location parameter, optionally with an indication of a time and/or date (e.g., time/date stamp).

There may be multiple central ML models, for example, one central ML model per central location. Each central ML model may be trained using a respective central dataset including data for the respective central location.

Some exemplary central location parameters are now described. It is noted that the central location parameters may correspond to remote location parameters, and/or alternatively and/or additionally be remote location parameters.

Optionally, for the case of allocation of computing and/or network resources, at least one of the central location parameters of the central location includes an indication of compatibility between components, for example, compatibility between versions and/or compatibility between vendors and/or compatibility between components (e.g., protocols), of hardware, software, and/or virtual resources. The compatibility may be a constraint on the allocation of the resources. Resources of different versions, vendors, and/or components may not necessarily work together, and may requiring certain groupings in order to function.

Optionally, for the case of allocation of people (e.g., employees), at least one of the central location parameters of the central location includes an indication of team group (e.g., social) networks of subsets of the resources (e.g., members of a work team, a group of friends, and/or an ad-hoc committee temporarily setup), and birthday or special event of one of the subset of resources of a certain team group (e.g., social) network. The parameters may indicate compatibility between the people, for example, ability to work together and/or preference to be allocated together. The team group may represents a constraint on the allocation, where the main ML model attempts computes the allocation of as many of the resources of each team group to the central location during a same time interval, where the time interval may be a further constraint. The team group may be represented by and/or correspond to multiple remote location parameters of multiple resources, for example, an indication that the respective resource is a member of the respective team group.

Optionally, for the case of allocation of people (employees), at least one of the central location parameters of the central location includes a canteen menu (i.e., what food is being served that day at the central location) and/or special event time intervals (e.g., birthday, guest, client meeting, special presentation, team building day). The canteen menu may be represented by and/or correspond to multiple remote location parameters of multiple resources, for example, preference for the food being served of the person. The main ML model may attempt to match the preferences for the food of the resource with the food being served on a certain day and allocate the respective resource to the central location on the day the food is being served.

At 104, multiple respective remote ML models are trained and/or provided. Each remote ML model corresponds to a respective resource and to one remote location. Each respective remote ML model is trained on a respective remote training dataset of historic remote location parameters for the respective resource and/or the respective remote location.

The historic dynamically adjusted remote location parameters may be represented, for example, a time sequence of values of the respective remote parameter, which varies over time. In another example, the historic dynamically adjusted remote location parameter may be represented, for example, as a value of the respective remote location parameter, optionally with an indication of a time and/or date (e.g., time/date stamp).

Some exemplary remote location parameters are now described. It is noted that the remote location parameters may correspond to central location parameters, and/or alternatively and/or additionally be central location parameters.

Optionally, for the case of allocation of computing and/or network resources, the remote location parameters may include a resource parameter including resource specific parameters of the resource associated with the respective location, for example, version, manufacturer, supported protocols, backwards compatibility, supported features, and the like.

Optionally, for the case of allocation of people (e.g., employees), the remote location parameters include a resource profile including at least one resource specific parameter of the resource associated with the respective remote location (e.g., a personal profile including personal parameters of the person). Examples of resource specific parameters include: seniority, tenure, salary, insurance data, commute cost data, gender, age, marital status, number of children, ages of children, demographic information, salary, and the like.

Optionally, for the case of allocation of computing and/or network resources, at least one of the remote location parameters of the respective remote location is based on network transport times, delays, and/or error encountered for data traffic transported between the respective remote location and one or more central locations. For example, between a certain client terminal and a certain server.

Optionally, for the case of allocation of people (e.g., employees), at least one of the remote location parameters of the respective remote location is based on commute between the remote and central locations, for example, distance from the respective remote location to the central location, historical estimated commute time from the remote location to the central location, predicted future commute time from the respective remote location to the central location, and preferred mode of transport.

At 106, a main ML model is provided and/or trained. The main ML model is trained on a main training dataset including training values for the central location parameters of the central location which may be obtained as an outcome of the central ML model (and optionally manually corrected as described herein), and for each of multiple sample resources, training values for the remote location parameters which may be obtained as an outcome of the respective remote ML model (and optionally manually corrected as described herein), and corresponding labels of allocation to the remote location or to the central location for each historical time interval.

Optionally, the main ML model includes multiple sub-ML models, each trained on a respective training dataset of a respective central location and corresponding set of one or more remote locations. Different data may be designed for being inputted into each respective sub-ML models. Outcomes of one or more sub-ML models may be fed as input into other sub-ML models. The outcome may be of a certain sub-ML model, and/or generated as a combination of multiple sub-ML models, for example, an average, the largest value, and/or computed by code such as a classifier and/or final sub-ML model.

At 108, a prediction of central location parameters of the central location(s) is received. The central location parameters of the central location(s) may be obtained as an outcome of the central ML model(s).

The outcome of the central location parameters may be generated, for example, on a predefined time interval (e.g., per day, per week) and/or triggered by an event (e.g., a significant change in input value(s)). The outcome may be, for example, a time sequence for a future time interval, for example, variable and/or constant values per day for the upcoming week.

Optionally, the central location parameter(s) includes at least one global constraint denoting a constraint on the resources allocated to the central location for one or more future time interval. The global constraint is inputted into the main ML model, and the allocation of the subset of the resources by the main ML model is done to satisfy the constraint. The constraint may be a social distancing requirement during a viral disease outbreak (e.g., COVID-19) defining, or example, a maximal density of resources at the central remote location, minimal distance between resources at the central remote location, maximal total number of resources at the central remote location, maximal number of resources at the central location and/or maximal number of resources per room at the central remote location. In another example, the global constraint includes planned future meetings scheduled to occur in the central location. The constraint may include an indication of whether to absolutely meet the constraint (e.g., must not exceed 10 people at the office), or to have a best effort and meet the constraint as best as possible (e.g., try to limit to 10, but 11 or 12 is also OK).

At 110, a respective prediction of remote location parameters is received for each respective remote location (corresponding to each resource). Each set of respective remote location parameter(s) is received as an outcome of a respective remote ML model of the respective remote location.

Each set of remote location parameters may be generated, for example, on a predefined time interval (e.g., per day, per week) and/or triggered by an event (e.g., a significant change in input value(s)). The outcome may be, for example, a time sequence for a future time interval, for example, variable and/or constant values per day for the upcoming week.

Optionally, the remote location parameter(s) include at least one constraint on the respective resource allocated to the central location or to the remote location for a certain future time interval, for example, number of remaining compulsory remote location time intervals. The constraint is inputted into the main ML model, and the allocation of the subset of the resources by the main ML model is done to satisfy the constraint. The constraint may include an indication of whether to absolutely meet the constraint (e.g., must meet all 10 compulsory days at the remote location, or to have a best effort and meet the constraint as best as possible (e.g., try to meet all 10 days, but 8 or 9 days is also OK).

Optionally, the remote location parameter(s) includes, for the respective resource (corresponding to the respective ML model), one or more of: a request for allocation of the respective resource to the remote location or the central location for the future time interval.

At 112, additional data parameters may be obtained and/or computed. The additional data parameters may be computed, for example, from historical outcomes of one or more ML models of the ensemble, and/or from datasets storing historical data, and/or other sources.

The additional data parameters may be for the central location, for certain remote locations, for all remote locations, and/or other data.

The additional data parameters may be inputted into the main ML model, optionally in combination with the central location parameters and/or the remote location parameters.

Examples of additional data parameters computed per resource (i.e., per corresponding remote location) include: number of accepted and/or declined allocations to an allocation request made by the respective resource, number of accepted and/or declined allocated to the request from a waiting list, number and/or time intervals of historical requests, pendency between the request and being granted the request, number of historical requests that were met, number of lack of meeting the request due to external factors.

An example of additional data parameter(s) that impacts all resources includes at least one scheduled event planned for a certain future time interval. For the case of allocation of computer and/or network resources, the scheduled event may be, for example, an upgrade of hardware that requires downtime, and/or a maintenance activity that requires downtime. For the case of allocation of people (e.g., employees), the scheduled event may be independent of the central location, for example, a conference being attended by some resources. The scheduled event impacts the allocation, since for example, resources attending the conference should not be allocated to the central location on the day of the conference. The scheduled event may be determined, for example, by analyzing calendar data of calendar applications used by the resources.

An example of additional data parameter(s) for each respective resource, is an indication of productivity of the respective resource at the remote location and/or the at the central location. The indication of productivity may be automatically computed, for example for the case of computing resources, as network bandwidth utilization, processor utilization, memory utilization, and data storage utilization. The indication of productivity may be automatically computed, for example for the case of allocation of people (e.g., employees), by accessing billing information to determine billings done from the remote and/or the central location, and/or determining amount of work completed at the remote and/or central location (e.g., number of lines of code written, number of telephone calls answered, and using other work measurements). The indication of productivity may be used by the main ML model for performing the allocation for maximizing productivity at the remote location and/or central location.

Other exemplary additional data parameters include one or more of:

Historical working location assignments and preferences:
1) working location preferences by date for the following n days;
2) history of working location assignment for each employee.

Calendar data:
1) in-office meetings/events date-time data;
2) out-of-office meetings/events date-time data;
3) virtual meetings, e.g. if the location is virtual space zoom, slack, skype, webex, and the like.
4) out-of-office personal events, vacations, sick days, emergencies;
5) country wide events, e.g. emergencies, quarantines etc.

Office infrastructure and costs:
1) number of available and adjusted for a given employee workplaces/workstations at the company's main office;
2) number of available and adjusted for a given employee workplaces/workstations at the company's branch or affiliated offices, partner coworking spaces;
3) average office specific furniture costs;
4) average office specific hiring costs (per employee);
5) available parking spots;

6) scheduled maintenance (e.g., construction work, network, computer system);
7) utilities downtime (e.g., shut off water, shut off electricity);
8) Transportation costs.

Employee characteristics:
1) seniority (intern, junior, middle, senior, management);
2) tenure at the company;
3) trial-period status;
4) salary;
5) company sponsored insurance information (medical, commute insurance);
6) company sponsored commute cost information;
7) the total number of compulsory home-office days according to the employment contract or collective agreement;
8) the number of used compulsory home-office days according to the employment contract or collective agreement;
9) insurance (e.g., life, medical, damage, car).

Employee productivity:
1) productivity when working from home;
2) productivity when working from office;
3) key performance indicators (KPI);
4) objective and key results (OKR).

Employee personal data:
1) Family
a. gender;
b. age;
c. marital status;
d. number of children;
e. ages of children;
2) Social network within office:
a. in-office friend list;
b. friends working location history;
c. friends birthday calendar;
d. personal events in close proximity from office location during prediction (testing) period;
e. team membership.
3) Commute specific:
a. distance from home to office;
b. historical/average/estimated commute duration;
c. commute traffic congestion prediction;
d. preferred mode of transportation (public transport, personal vehicle, carpooling, walking, biking etc.);
4) Working location preferences and StayHome specific data:
a. number of accepted/declined of assignments of working location;
b. number of accepted/declined of assignments of working location if selected from the waiting list;
c. number and dates of preferred working location changes;
d. pendency (days between) working location preference assignment and its changes;
e. number of meeting schedule and location changes due to working location actual and preferred assignment mismatch;
f. number of working location preference and actual assignment matches.
5) Office location benefits data:
a. office canteen menu;
b. office training/event dates;

At 114, the central location parameters of the central location, the remote location parameters of the certain remote location of the respective resource (and/or of multiple resources), and optionally the additional data parameters, are inputted into the main ML model.

Optionally, a feature vector is created from a combination of the central location parameters and/or the remote location parameters and/or the additional data parameters, for example by concatenation. The feature vector may be inputted into the main ML model.

Optionally, the central location parameters and/or the remote location parameters and/or the additional data include a time sequence of values for multiple historical time intervals.

Optionally, one or more features may be extracted from the central location parameters and/or the remote location parameters and/or the additional data parameter(s). The extracted features and/or raw features may be inputted into the main ML model.

At 116, an allocation of the respective resource to the remote location or to the central location for one or more future time intervals is obtained as an outcome of the main ML model. The main ML model allocates one subset of the resources to respective remote location(s), and another subset to the central location(s).

Optionally, each remote location is allocated no more than a single resource. The central location is allocated multiple sample resources. It is noted that in some cases, no resources may be allocated to one or more remote locations. In some cases, a single resource may be allocated to the central location. In some cases, no resources may be allocated to the central location. The central location may be converted into a remote location and/or a suggestion may be made to convert the central location to the remote location (e.g., to a user), for example, by definition (e.g., of a user) and/or automatically by code, for example, when no more than one resource is continuously allocated to the central over a requirement (e.g., over a month, or 3 months, or more). The remote location may be converted into a central location and/or a suggestion may be made to convert the remote location to the central location (e.g., to a user), for example, by definition (e.g., of a user) and/or automatically by code, for example, when multiple resources are attempted to be allocated to the same remote location over a requirement (e.g., more than 5 times, or 10 times, or other numbers). Optionally, the number of remote locations and/or central locations is adjusted, for example, increased and/or decreased, for example, a suggestion is made (e.g., to a user), as defined (e.g., by a user), and/or automatically by code, for example, based on an analysis of previous allocation patterns. For example, when the central location has too many resources allocated to it, another central location may be created. When some remote locations do not have any resources allocated to them (e.g., for over a month) those remote locations may be removed.

Optionally, the allocation of the respective resource is for each of multiple time intervals, for example, allocation each day of the upcoming week. For example, a certain resource is allocated to the central location on Monday and Thursday, and to the remote location on Tuesday, Wednesday, and Friday.

Optionally, the allocation of the respective resource is based on a numerical score indicative of a ranking likelihood of being allocated to the remote location or to the central location. The resources may be allocated and ranked according to the respective numerical score. Resources not allocated to the remote location or the central location (e.g., as the respective resource may have requested) may be placed on a waiting list according to the numerical score.

Alternatively or additionally, the main ML model may generate other outcome(s). Optionally, when costs associated with the central location and/or costs associated with each resource at the central location, and/or costs associated with resources are remote locations are inputted into the main ML model, the ML model may compute the allocation for reducing the subset of central location parameters and/or generate a recommendation for obtaining the reduction of costs by implementing the computed allocation.

At 117, the respective resource (e.g., each respective resource) is allocated to the remote location or to the central location for the one or more future time intervals according to the outcome of the main ML model.

At 118, one or more features described with reference to 108-117 may be iterated for each respective resource. Alternatively or additionally, one or more features described with reference to 108-116 may be implemented simultaneously or multiple resources.

Optionally, the accuracy of one or more outcomes (e.g., predictions) of one or more ML models of the ML model ensemble may be evaluated, for example, using an average prediction accuracy metric for each of the resources based on actual assigned locations. The accuracy metrics (errors) may include: 1) mean absolute error; 2) mean squared error; 3) accuracy ratio (mean absolute percentage error); 4) logarithmic loss; 5) area under the curve.

At 120, the features described with reference to 102-118 may be dynamically iterated using updated central location parameters and/or remote location parameters and/or additional data, for additional future time intervals.

Optionally, outcomes of some ML models are provided as input into other ML models, for example, one or more of:
  Feeding a previous outcome of the central ML model as input into at least one of the remote ML models for generating the respective outcome of the respective remote ML model.
  Feeding a previous of the main ML model as input into at least one of the remote ML models for generating the respective outcome of the respective remote ML model.
  Feeding one or more previous outcomes of one or more remote ML models as input into at least one other remote ML models for generating the respective outcome of the respective remote ML model.
  Feeding a previous outcome of one or more remote ML models as input into the central ML model for generating the outcome of the central ML model.
  Feeding a previous outcome of the main ML model as input into the central ML model for generating the outcome of the central ML model.
  Feeding a previous outcome of the main ML model as current input into the main ML model for generating the outcome of the main ML model.
  Feeding a previous outcome of the respective remote ML model as current input into the respective remote ML model for generating the outcome of the remote ML model.
  Feeding a previous outcome of the central ML model as current input into the central ML model for generating the outcome of the central ML model.

Referring now back to FIG. 3, at 302, training values for central location parameters of the central location, are received. Exemplary central location parameters are described herein. A central training dataset is created from the training values.

The central training dataset and/or remote training dataset and/or main training datasets described herein may relate, for example, to a certain set of defined central and/or remote resources, for example, of a certain entity (e.g., data storage provider, company), and/or a certain technical architecture (e.g., cloud storage and client terminals, working from home or office). In such implementation, the created ML model ensemble denotes a customized ML model ensemble for the certain entity and/or certain technical architecture. Alternatively, data is aggregated from central training dataset and/or remote training dataset and/or main training datasets of different sources, for example, multiple entities (e.g., multiple data storage provides, multiple companies), which may be of a similar technical architecture and/or different technical architectures. Aggregating data from multiple sources may provide additional data which may improve the allocation (e.g., accuracy of allocation) of the created ML model ensemble, which may be used by each of the multiple sources.

At 304, one or more central ML model(s) are trained using the central training dataset.

At 306, 302 and 304 are iterated, for example, the central training dataset is updated, and the central ML model is re-trained.

Optionally, the central training dataset is updated using one or more of: inserting a previous outcome of one or more remote ML models as input into the central training datasets for updating training of the central ML model, inserting a previous outcome of the central ML model as current input into the central training datasets for updating training of the central ML model, and inserting a previous outcome of the main ML model as input into the central training datasets for updating training of the central ML model.

At 308, training values for respective remote location parameters of one or more respective remote location, are received. Exemplary remote location parameters are described herein. Respective remote training datasets are created from the respective training values.

At 310, multiple remote ML models are each trained using a respective remote training dataset.

At 312, 308 and 310 are iterated, for example, respective remote training datasets are updated, and the respective remote ML model is re-trained.

Optionally, each respective remote training dataset is updated using one or more of: inserting a previous outcome of the central ML model as input into at least one of the remote training datasets for updating training of the respective remote ML model, inserting a previous outcome of the main ML model as input into at least one of the remote training datasets for updating training of the respective remote ML model, and inserting one or more previous outcomes of one or more remote ML models as input into at least one other remote training datasets for updating training of the respective remote ML model.

At 314, the central location parameter outcomes of the central ML model and/or the remote location parameters of respective remote ML models and/or central location parameters from other sources and/or remote location parameters from outer sources are received. Additional data parameters may be received, as described herein. A main training dataset is created from the central location parameter, the remote location parameters for each of the sample resources (i.e., the corresponding remote locations) and/or from the additional data parameters.

At 316, a main ML model is trained using the main training dataset.

At 318, 314 and 316 are iterated, for example, the main training dataset is updated, and the main ML model is re-trained.

Optionally, the main training dataset is updated using one or more of: inserting a previous outcome of the main ML model as current input into the main training datasets for updating training of the main ML model, and inserting a previous outcome of the respective remote ML model as current input into the respective remote training datasets for updating training of the remote ML model.

Optionally, the main training dataset is updated with a manual indication of allocation of respective sample individual(s) to the central location or the remote location is received when a previous allocation outcome of the main ML model is incorrect. The manual indication may be included in the main training dataset, for updating the main ML model.

At 320, the ML model ensemble, including the remote location ML models, the central location ML model, and/or the main ML model, is provided.

Referring back to FIGS. 4A-4D, the example depicted may be for the case of allocation of people (e.g., employees) to work from remote locations (e.g., home) and/or from central locations (e.g., office). However, FIGS. 4A-4D may be used for allocation of other resources, for example, computer and/or network resources, as described herein.

Figure 4A:
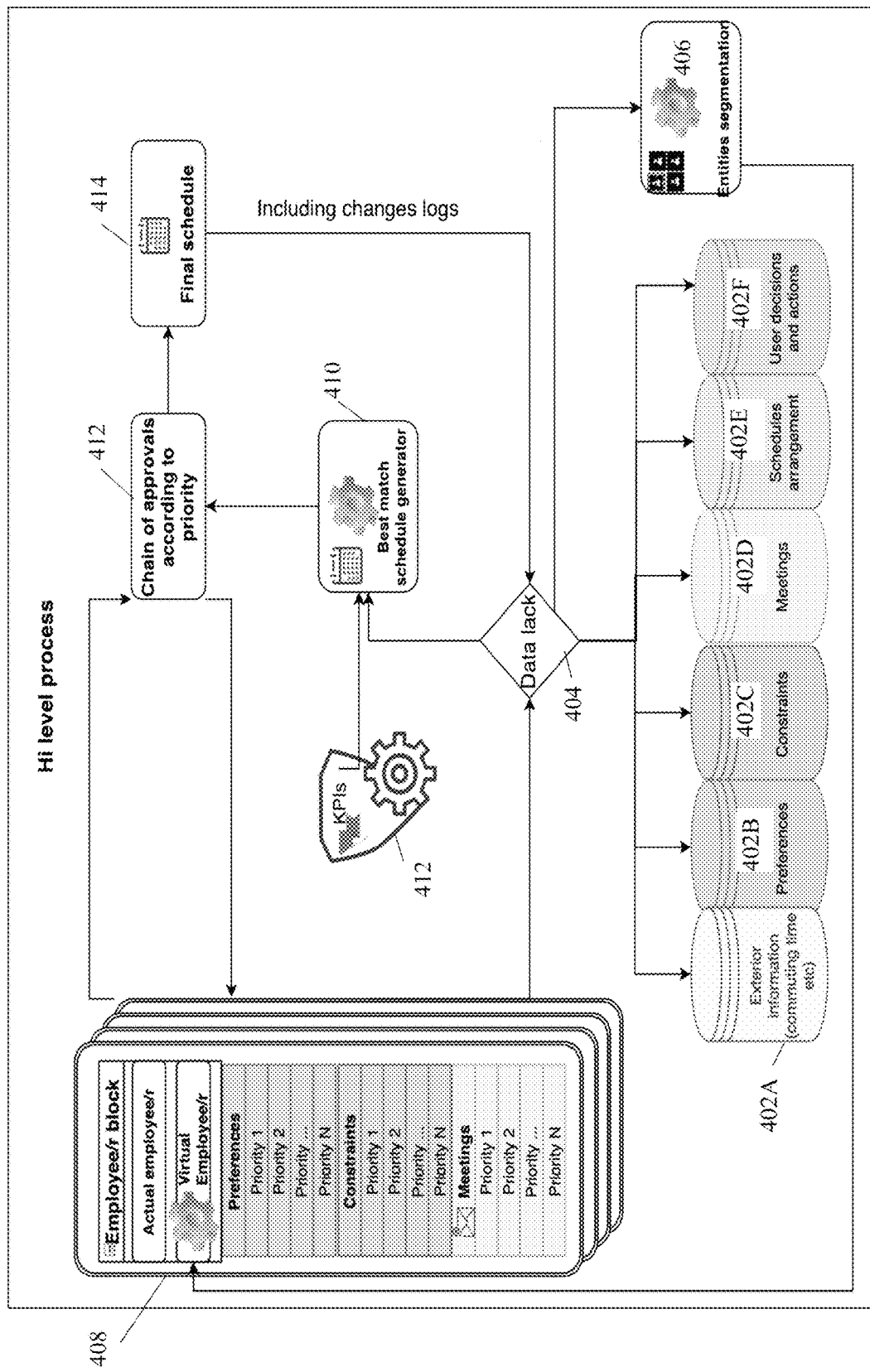
FIGS. 4A-4D are flowcharts of an exemplary process for allocation of resources to a remote location or to a central location, in accordance with some embodiments of the present invention.

FIG. 4A process an overall high level dataflow, including main ML model components of the ML model ensemble, and dataflow between the ML model components. Data repositories (e.g., datasets) 402A-F store current and/or historical parameters, which may be dynamically updated. The parameters may be local and/or remote parameters, as described herein. The stored parameters may be fed into components of the ML model, as described herein. For example, dataset 402A stores an indication of exterior information (e.g., commute time), dataset 402B stores an indication of preferences of the resources, dataset 402C stores an indication of constraints, dataset 402D stores an indication of meetings, dataset 402E stores an indication of schedules arrangements, and dataset 402F stores an indication of user decisions and/or actions. Other dataset may be implemented, for example, as described herein.

Datasets 402A-F may store dynamically changing data, and/or static data.

At 404, a data lack ML component may encode parameters stored in datasets 402A-F, for example, for certain time intervals, and/or as a sequence of multiple values over time. Data lack ML component may be implemented, for example, as a recurrent neural network (RNN) which is designed to encode dynamic input data into a state. Data lack ML model may generate an ad-hoc ensemble of static parameters stored in datasets 402A-F.

At 406, an entities segmentation ML component may aggregate the parameters encoded from datasets 402A-F into different entities (e.g., resources), for example, corresponding to remote locations and/or different people (e.g., employees) and/or different resources. The encoded data may be segmented per central and/or remote location.

At 408, the encoded segmented parameters (e.g., multiple preferences, constraints, meetings, and the like) of the respective resources and/or the central and/or remote locations may be inputted into a corresponding remote and/or central ML model. The "virtual employee/r" denotes the respective remote and/or central ML models, which are trained to learn how the "real" employee and/or employer make actions based on current and/or historical data, for example, trained on the outcomes of the real employee/r used as ground truth labels of the datasets 402A-F, as described herein.

The outcomes of the remote and/or central ML models 408 is fed back to data lack ML model 404, for dynamically updating datasets 404A-F, for iterative feeding as input into other central and/or remote ML models 408, as described herein.

The outcomes of the remote and/or central ML models 408 is fed into a best match schedule generator ML model 410, also referred to herein as main ML model 410, as described herein. Additional data may be fed into main ML model 410, for example, key performance indicators (KPI) 412, and/or other data from datasets 402A-F and/or other data, for example, as described herein.

Main ML model 410 generates an outcome of an allocation of the respective resource to the central or remote location, as described herein.

At 412, the allocation outcomes obtained from the mail ML Model 410 may undergo a re-evaluation, for example, a manual review by a user. The re-evaluation may be stored as a ground truth label, and used for re-training and/or updating remote and/or central ML models 408, for example, as described herein.

At 414, a final allocation is obtained based on the re-evaluation. The final allocation may be stored as a ground truth label, and used for re-training and/or updating main ML model 410, and/or stored in datasets 402A-F, for example, as described herein.

Figure 4B:
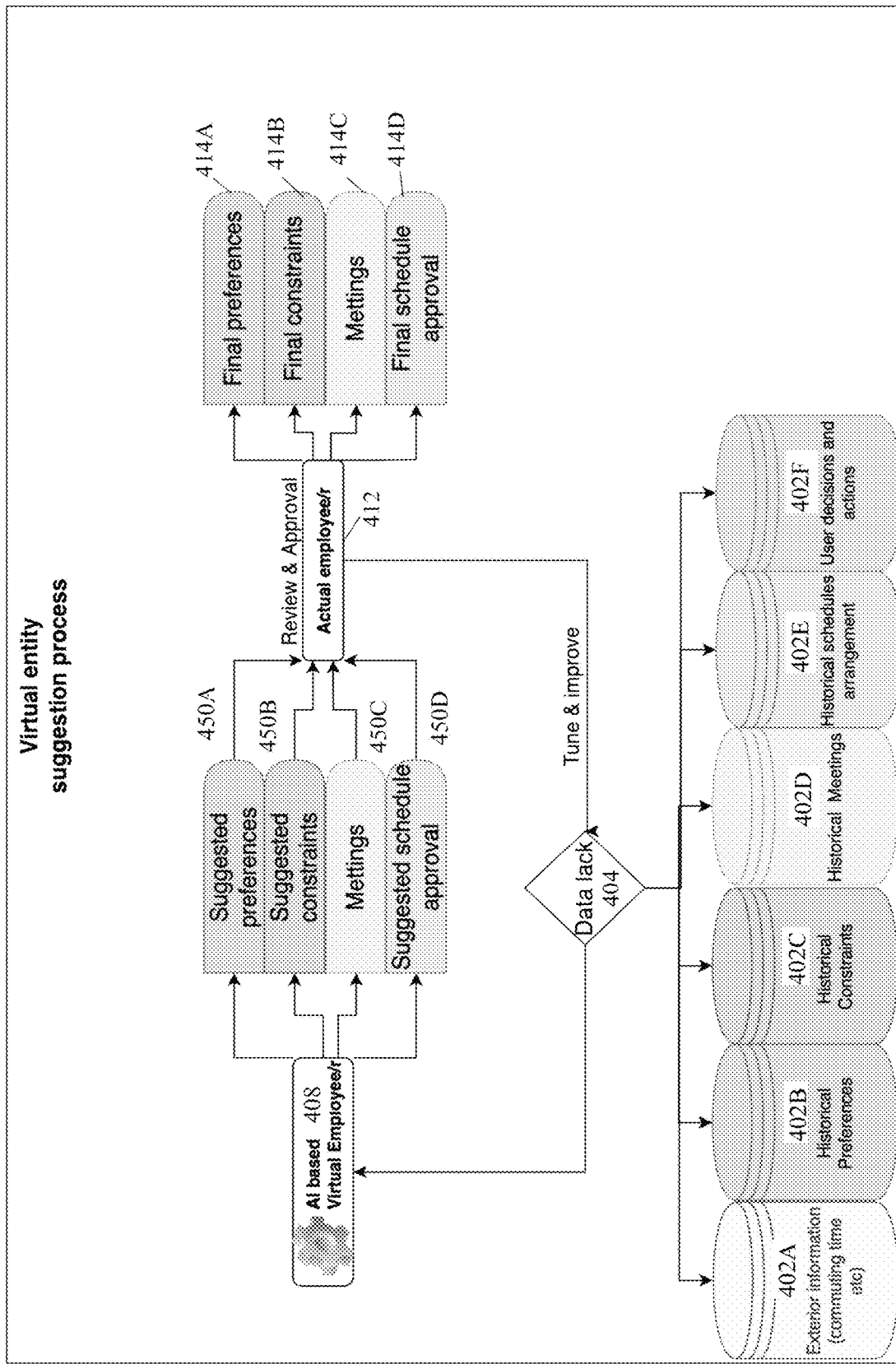

FIG. 4B is an exemplary dataflow with respective to a certain central and/or remote ML model 408, also referred to herein as AI based virtual employee/r 408. As described herein, there are multiple central and/or remote ML models, where certain ML model 408 is an example of one, shown for clarity. As described herein, data is inputted into the certain central and/or remote ML model 408, for example one or more of: encoded data, for example, static values and/or a time sequence (e.g., state), obtained from datasets 402A-F, as outcomes of other central and/or remote ML models, as outcome of the same certain central and/or remote ML model 408, as outcome of the main ML model, and/or additional data and/or additional parameter, for example, as described herein.

Certain central and/or remote ML model 408 outputs a prediction of respective central and/or remote parameters (as described herein), for example, suggested preferences 450A, suggested constrains 450B, meetings 450C, and/or suggested schedule approval 450D.

At 412, parameters 450A-D may undergo a re-review, optionally a manual review, for example, by an actual human employee/r. The re-review may adjust the outcomes generated by ML model 408. The results of the re-review may be denoted as final results, for example, final preferences 414A, final constrains 414B, meetings 414C, and final schedule 414D. The final results may be fed into the main ML Model for allocation of the resources to the central and/or remote location. The final results may be used to update and/or re-train the certain ML model 408 and/or other ML models, for example, by being used as ground truth as a re-label of the outcomes of the ML model 408 and/or as new data, for example, as described herein.

Figure 4C:
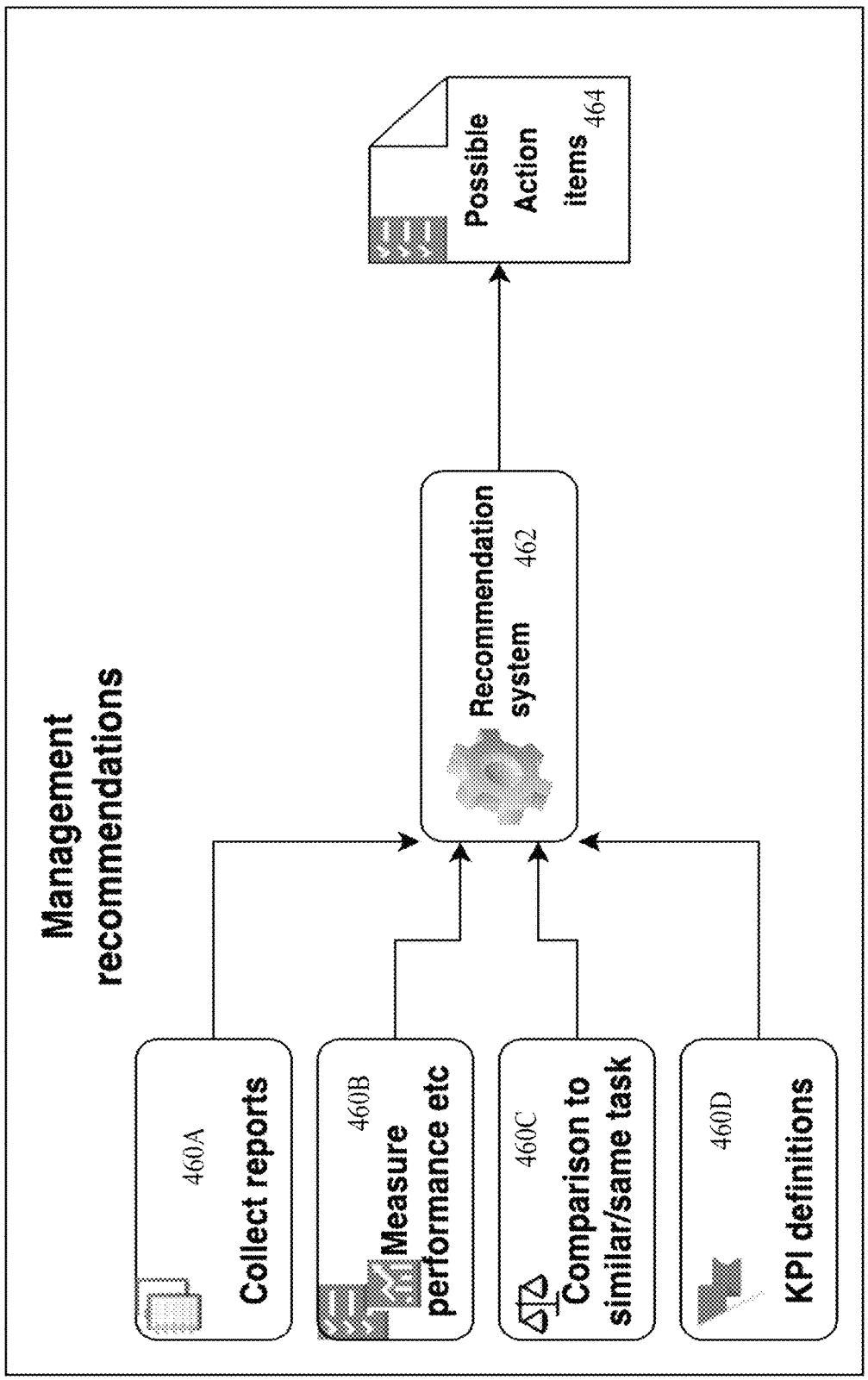

FIG. 4C is an exemplary dataflow of a central ML model, sometimes referred to herein as a recommendation system 462. Central ML model receives as input, for example one or more of, reports 460A which may be automatically collected, performance measures 460B (e.g., of resources), a comparison to similar/same tasks 460C, KPI definitions 460D, outcomes of the remote ML models, outcomes of the main ML Model, outcomes of other central ML models, outcome of the same ML model, and/or other data and/or other parameters, as described herein. Central ML model 462 may generate an outcome of possible action items 464, for example, central location parameters and/or other predictions, for example, as described herein.

Figure 4D:
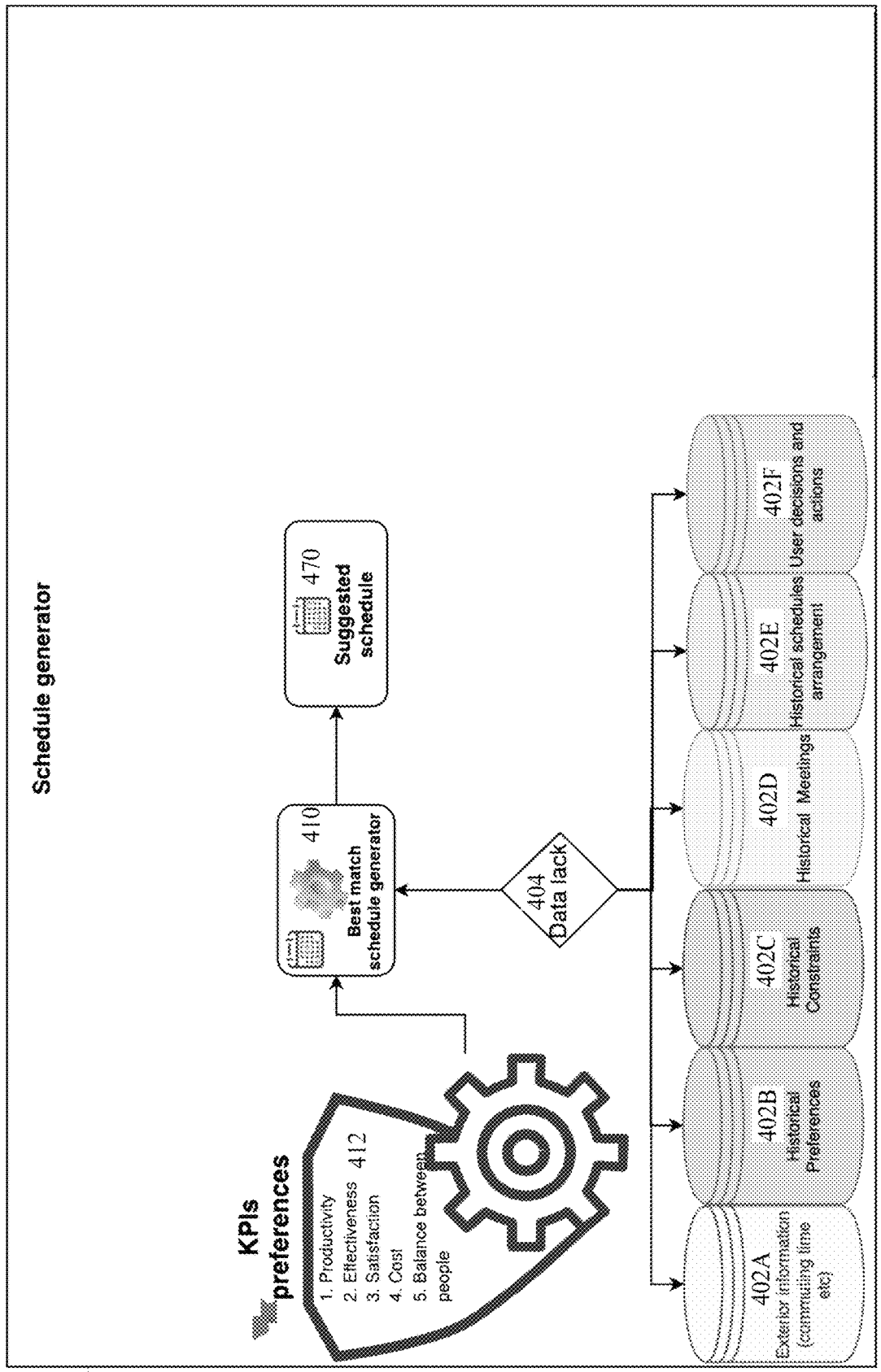

FIG. 4D is an exemplary dataflow of a main ML model 410, sometimes referred to herein as a best match schedule generator 410. Main ML model 410 receives as input, for example, one or more of: outputs of remote ML models, output(s) of central ML model(s), previous output of the main ML model, KPI preferences 412 (e.g., productivity, effectiveness, satisfaction, cost, and/or balance between people), datasets 402A-F, and/or other data and/or other parameters, as described herein. Main ML model 410 generates an outcome of suggested schedule 470, which is a proposed allocation of the resources to the central and/or remote locations. As described herein, the suggested schedule 470 may be adjusted, where the adjustment and/or the non-adjustment is used to update and/or re-train and/or update one or more of: the main ML Model, remote ML models, and/or central ML model(s).

Examples of implementations of at least some embodiments described herein is now provided. It is noted that portions of the examples may be implemented with embodiments, for example, data structure inputs and/or outputs.

Example 1

The main ML model generates an outcome indicative of a recommendation to the resource (e.g., employee, employer, manager) the upcoming week allocation schedule (i.e., to the central location or to the respective remote location) based on similar resources' history. The data may be pre-processed as follows, using one or more of:
  Group by 'time windows' so that the day-status of every week is the prediction (the output of the main model) based on the previous week(s).
  Group by resource id
  Each ML model (i.e., the central ML model and/or the remote ML model) of the ML model ensemble may be constructed of the following exemplary components: two input streams, processing layers and one stateful output.

The two different inputs into the ML models of the ML model ensemble may be adjusted to be able to handle: Meta data (e.g., configurations), parameters of each resource; Time series data (the records of each day), the different status (e.g., the initial status, the modifications and the final status) of each date in a breakdown by weeks of the historical records, each 'day status' record is part of a tuple with who/what created this record.

The processing portion in the ML model ensemble may be a combination of Long short-term memory (LSTM) layers with self-attention based layers for the time series data, dense and/or concatenate layers in order to combine the meta data input.

The output of the main ML model is the prediction and/or suggestion of the customized allocation schedule for the upcoming week for each resource, in granularity of days. Final day status of the following week.

Exemplary inputs (e.g., into the ML model ensemble and/or for training the ML model ensemble):
  Examples of general input fields (The configuration of 'enabled' refers to "whether to consider in the prediction or not"), where Entity refers to employee resources and corresponding remote ML models, Manager refers to the main ML model, Office refers to the central ML model, and settings refers to corresponding parameters which are used as input and/or outputs and/or included in the training dataset(s): Entity id, Manager id, Entity settings—office calendar events enabled, Entity settings—minimum stay home time, Entity settings—minimum stay home time enabled, Entity settings—maximum stay home time, Entity settings—maximum stay home time enabled, Manager settings—Kpi control type (use/ignore productivity enabled, quality enabled, productivity enabled), Manager settings Commuting time enabled, Manager settings—Office calendar events enabled, Manager settings—Productivity enabled, Manager settings—Quality enabled, Manager settings—Effectiveness enabled, Manager settings—minimum waiting list, Manager settings—minimum waiting list enabled, Manager settings—maximum waiting list, Manager settings—maximum waiting list enabled, Manager settings—Entity confirm expiration, Manager settings—waiting list enabled, Manager settings—Entity home office status enabled, Manager settings—passed stay home days enabled, Office settings—days off in a week, Office settings—days off in the office, Office settings—shift start time, Office settings—shift end time.

Examples of List of input fields for each historical 'time window' (as much as available): The different status (e.g., the initial status, the modifications and the final status) of each date in a breakdown by weeks of the historical records, each 'day status' record is part of a tuple with who/what created this record, Entity update for each day—quality, Entity update for each day—effectiveness, Entity update for each day—productivity, Entity update for each day—commuting time, Manager update for each day—quality, Manager update for each day—effectiveness, Manager update for each day—productivity, Date, Office calendar events, Historical final days' status of the Entity (if the entity actually was at home/office).

The output generated by the main ML model may be, for example, a matrix of 5, 6, 7 days (i.e., the following week) over 128 status ($2^7$) in order to give the probabilities for each possible day's combination in the week.

Example 2

The main ML model generates an outcome indicative of a recommendation to the resource (e.g., employee, employer, manager), the automatic replies to the proposed schedule based on similar resource' history.

The data may be pre-processed as follows, using one or more of:
  Group by 'time windows' so that the day-status of every week will be the prediction (the output of the main ML model) based on the previous weeks.
  Group by resource id.
  Each ML model (i.e., the central ML model and/or the remote ML model) of the ML model ensemble may be constructed of the following exemplary components: three input streams, processing layers and one stateful output.

The three different inputs into the ML models of the ML model ensemble may be adjusted to be able to handle: Meta data (e.g configurations), parameters of each entity, Time series data (the records of each day), the different status (e.g., the initial status, the modifications and the final status) of each date in a breakdown by weeks of the historical records, each 'day status' record is part of a tuple with who/what created this record, Fixed structure data, the upcoming potential schedule for each resource (e.g., a vector of 7 binary cells), the upcoming suggested schedule with all the past modifiers of the days' status (i.e., the additional input in comparison to Example #1).

The processing portion in the ML model ensemble is a combination of LSTM layers with self-attention based layers for the time series data, dense and/or concatenate layers in order to combine the meta data input.

The output of the main ML model includes the approvals, rejections and/or suggestions for the upcoming allocation schedule.

Exemplary inputs (e.g., into the ML model ensemble and/or for training the ML model ensemble):

Examples of general input fields (The configuration of 'enabled' refers to "whether to consider in the prediction or not"), where Entity refers to employee resources and corresponding remote ML models, Manager refers to the main ML model, Office refers to the central ML model, and settings refers to corresponding parameters which are used as input and/or outputs and/or included in the training dataset(s): Entity id, Manager id, Entity settings—office calendar events enabled, Entity settings—minimum stay home time, Entity settings—minimum stay home time enabled, Entity settings—maximum stay home time, Entity settings—maximum stay home time enabled, Manager settings—Kpi control type (use/ignore productivity enabled, quality enabled, productivity enabled), Manager settings—Commuting time enabled, Manager settings—Office calendar events enabled, Manager settings—Productivity enabled, Manager settings—Quality enabled, Manager settings—Effectiveness enabled, Manager settings—minimum waiting list, Manager settings—minimum waiting list enabled, Manager settings—maximum waiting list, Manager settings—maximum waiting list enabled, Manager settings—entity confirm expiration, Manager settings—waiting list enabled, Manager settings—entity home office status enabled, Manager settings—passed stay home days enabled, Office settings—days off in a week, Office settings—days off in the office, Office settings—shift start time, Office settings—shift end time.

Examples of List of input fields for each historical 'time window' (as much as available): The different status (e.g., the initial status, the modifications and the final status) of each date in a breakdown by weeks of the historical records, each 'day status' record is part of a tuple with who/what created this record, Entity update for each day—quality, Entity update for each day—effectiveness, Entity update for each day—productivity, Entity update for each day—commuting time, Manager update for each day—quality, Manager update for each day—effectiveness, Manager update for each day—productivity, Date, Office calendar events, Historical final days' status of the entity (if the entity actually was at home/office), List of input fields for the upcoming week: Day in week, Status.

The output generated by the main ML model may be, for example, a vector of 7 binary cells (the upcoming week), which reflect the upcoming schedule after the review of the entity.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant machine learning models will be developed and the scope of the term machine learning model is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method of training a ML model ensemble for dynamic allocation of resources to a remote location or to a central location, comprising:
    receiving a plurality of training values for a plurality of central location parameters of the central location;
    training a central ML model using the training values for the plurality of central location parameters;
    for each of a plurality of sample resources:
        receiving training values for a plurality of remote location parameters;
        training a respective ML model using the plurality of remote location parameters for the respective sample resource;
        receiving a manual indication of allocation of the respective sample resource to the central location or the remote location;
    creating a main training dataset including the plurality of training values for the plurality of central locations, and the training values for the plurality of remote location parameters for each of the plurality of sample resources labelled with the manual indication; and
    training a main ML model using the training dataset for allocating a resource to at least one central location or to the respective remote location, wherein a subset of a plurality of resources are allocated to respective remote locations and another subset of the plurality of resources are allocated to at least one central location.

2. The computer implemented method of claim 1, further comprising updating the training datasets using at least one member of a group comprising of:
    (i) inserting a previous outcome of the central ML model as input into at least one of the plurality of remote training datasets for updating training of the respective remote ML model;
    (ii) inserting a previous outcome of the main ML model as input into at least one of the plurality of remote training datasets for updating training of the respective remote ML model;
    (iii) inserting one or more previous outcomes of one or more remote ML models as input into at least one other remote training datasets for updating training of the respective remote ML model;
    (iv) inserting a previous outcome of one or more remote ML models as input into the central training datasets for updating training of the central ML model;
    (v) inserting a previous outcome of the main ML model as input into the central training datasets for updating training of the central ML model;
    (vi) inserting a previous outcome of the main ML model as current input into the main training datasets for updating training of the main ML model;
    (vii) inserting a previous outcome of the respective remote ML model as current input into the respective remote training datasets for updating training of the remote ML model; and
    (viii) inserting a previous outcome of the central ML model as current input into the central training datasets for updating training of the central ML model.

3. The computer implemented method of claim 1, wherein each remote location is allocated no more than a single sample resource, and the central location is allocated a plurality of sample resources.

4. A computer implemented method of dynamic allocation of a plurality of resources to a plurality of remote location or at least one central location using an ensemble of machine learning (ML) models, comprising:
    receiving, as an outcome of a central ML model, a prediction of a plurality of central location parameters of the at least one central location, wherein the central ML model is trained on a central training dataset of historic dynamically adjusted central location parameters;
    iterating for each respective resource of the plurality of resources:
        receiving, as an outcome of a respective remote ML model of a plurality of remote ML models, a prediction of a plurality of remote location parameters of a certain remote location, wherein each respective remote ML model corresponds to a respective resource and to one certain remote location, wherein the respective remote ML model is trained on a respective remote training dataset of historic remote location parameters;
        inputting the plurality of central location parameters of the at least one central location and the plurality of remote location parameters of the certain remote location of the respective resource into a main ML model; and
        obtaining, as an outcome of the main ML model, an allocation of the respective resource to the remote location or to the at least one central location for at least one future time interval, wherein a subset of a plurality of resources are allocated to respective remote locations and another subset of the plurality of resources are allocated to at least one central location,
    wherein the main ML model is trained on a main training dataset including: training values for the plurality of central location parameters of the central location, and for each of a plurality of sample resources, training values for the plurality of remote location parameters, and corresponding labels of allocation to the remote location or to the central location for each of at least one historical time intervals.

5. The computer implemented method of claim 4, further comprising at least one member of a group comprising of:
    (i) feeding a previous outcome of the central ML model as input into at least one of the plurality of remote ML models for generating the respective outcome of the respective remote ML model;

(ii) feeding a previous of the main ML model as input into at least one of the plurality of remote ML models for generating the respective outcome of the respective remote ML model;

(iii) feeding one or more previous outcomes of one or more remote ML models as input into at least one other remote ML models for generating the respective outcome of the respective remote ML model;

(iv) feeding a previous outcome of one or more remote ML models as input into the central ML model for generating the outcome of the central ML model;

(v) feeding a previous outcome of the main ML model as input into the central ML model for generating the outcome of the central ML model;

(vi) feeding a previous outcome of the main ML model as current input into the main ML model for generating the outcome of the main ML model;

(vii) feeding a previous outcome of the respective remote ML model as current input into the respective remote ML model for generating the outcome of the remote ML model; and (viii) feeding a previous outcome of the central ML model as current input into the central ML model for generating the outcome of the central ML model.

6. The computer implemented method of claim 4, wherein each remote location is allocated no more than a single resource of the plurality of resources, and the central location is allocated a plurality of sample resources.

7. The computer implemented method of claim 4, further comprising, allocating the respective resource to the remote location or to the at least one central location according to the outcome of the main ML model.

8. The computer implemented method of claim 4, wherein the features of the method are dynamically iterated using updated plurality of central location parameters and/or plurality of remote location parameters, for additional future time intervals.

9. The computer implemented method of claim 4, wherein at least one of the plurality of central location parameters and the plurality of remote location parameters comprises a time sequence of values for each of a plurality of historical time intervals.

10. The computer implemented method of claim 4, wherein the main ML model comprises a plurality of sub-ML models, each trained on a respective training dataset of a respective central location and corresponding plurality of remote locations, wherein the inputting is into the respective sub-ML models and the outcome is of the respective sub-ML models.

11. The computer implemented method of claim 4, further comprising:
receiving an indication of a manual adjustment to the allocation for the respective resource by the outcome of the ML model;
creating a training record, using the respective plurality of central location parameters of the central location, the plurality of remote location parameters of the certain remote location of the respective resource, and a label comprising the manual adjustment; and
updating the ML model using the training record.

12. The computer implemented method of claim 4, wherein the allocation of the respective resource is for each of a plurality of time intervals.

13. The method of claim 4, further comprising:
receiving, as an outcome of the central ML model, at least one global constraint as a certain central location parameter, the at least one global constraint denoting a constraint on the plurality of resources allocated to the central location for the at least one future time interval;
inputting the at least one global constraint into the main ML model,
wherein the allocation of the subset of the plurality of resources satisfies the constraint.

14. The method of claim 13, wherein the plurality of remote location parameters for the central location of each of the plurality of resources are inputted as a combination, with the at least one global constraint and with the plurality of central location parameters, into the main ML model.

15. The method of claim 13, wherein the at least one global constraint comprises a physical distancing requirement during a viral disease outbreak defining at least one of: a maximal density of resources at the central remote location, minimal distance between resources at the central remote location, maximal total number of resources at the central remote location, and maximal number of resources per room at the central remote location.

16. The method of claim 13, wherein the at least one global constraint comprises at least one member selected from the group consisting of: maximal number of resources at the central location, and compatibility between resources.

17. The method of claim 4, further comprising:
receiving, for the respective resource as an outcome of the respective remote ML model, at least one constraint on the respective resource allocated to the central location or to the remote location for the at least one future time interval;
inputting the at least one constraint into the main ML model,
wherein the allocation of the respective resource satisfies the constraint.

18. The method of claim 17, wherein the at least one constraint is selected from the group consisting of: number of remaining compulsory remote location time intervals.

19. The method of claim 4, wherein the allocation of the respective resource comprises a numerical score indicative of a ranking likelihood of being allocated to the remote location or to the central location, wherein resources not allocated to the remote location or to the central location are placed on a waiting list according to the numerical score.

20. The method of claim 4, further comprising:
receiving, for the respective resource as an outcome of the respective remote ML model, request for allocation to the remote location or the central location for the at least one future time interval;
wherein inputting further comprises inputting the request for allocation into the main ML model, wherein the main ML model computes the allocation for meeting the request.

21. The method of claim 4, further comprising receiving at least one additional data parameters for the respective resource, wherein the additional data is inputted into the main ML model, the at least one additional data parameters selected from the group consisting of: number of accepted and/or declined allocations to a request, number of accepted and/or declined allocated to the request from a waiting list, number and/or time intervals of historical requests, pendency between the request and being granted the request, number of historical requests that were met, number of lack of meeting the request due to external factors.

22. The method of claim 4, further comprising:
receiving, at least one scheduled event planned for a certain future time interval independent of the central location, the at least one schedule event impacting a plurality of resources;
wherein inputting further comprises inputting the at least one scheduled event into the main ML model, wherein the ML model computes the allocation for meeting the at least one scheduled event.

23. The method of claim 4, further comprising:
extracting a plurality of extracted features from at least one of the plurality of central location parameters, and the plurality of remote location parameters,
wherein inputting comprises inputting at least the plurality of extracted features into the ML model.

24. A system for dynamic allocation of a plurality of resources to a plurality of remote location or at least one central location using an ensemble of machine learning (ML) models, comprising:
at least one hardware processor executing a code for:
receiving, as an outcome of a central ML model, a prediction of a plurality of central location parameters of the at least one central location, wherein the central ML model is trained on a central training dataset of historic dynamically adjusted central location parameters;
iterating for each respective resource of the plurality of resources:
receiving, as an outcome of a respective remote ML model of a plurality of remote ML models, a prediction of a plurality of remote location parameters of a certain remote location, wherein each respective remote ML model corresponds to a respective resource and to one certain remote location, wherein the respective remote ML model is trained on a respective remote training dataset of historic remote location parameters;
inputting the plurality of central location parameters of the at least one central location and the plurality of remote location parameters of the certain remote location of the respective resource into a main ML model; and
obtaining, as an outcome of the main ML model, an allocation of the respective resource to the remote location or to the at least one central location for at least one future time interval, wherein a subset of a plurality of resources are allocated to respective remote locations and another subset of the plurality of resources are allocated to at least one central location,
wherein the main ML model is trained on a main training dataset including: training values for the plurality of central location parameters of the central location, and for each of a plurality of sample resources, training values for the plurality of remote location parameters, and corresponding labels of allocation to the remote location or to the central location for each of at least one historical time intervals.

* * * * *